United States Patent [19]

Shioiri et al.

[11] 4,424,158
[45] Jan. 3, 1984

[54] PROCESS FOR PREPARING TRIALKYLSILYLDIAZOMETHANES

[75] Inventors: Takayuki Shioiri, Aichiken; Toyohiko Aoyama; Shigehiro Mori, both of Nagoyashi, all of Japan

[73] Assignee: Chisso Corporation, Osaka, Japan

[21] Appl. No.: 401,268

[22] Filed: Jul. 23, 1982

[30] Foreign Application Priority Data

Jul. 23, 1981 [JP] Japan ................................ 56-115510

[51] Int. Cl.$^3$ ....................... C07D 201/00; C07F 7/10
[52] U.S. Cl. .......................... 260/239 AA; 260/239 A
[58] Field of Search .................... 260/239 AA, 239 A

[56] References Cited

FOREIGN PATENT DOCUMENTS 232256 5/1969 U.S.S.R. ....................... 260/239 AA

Primary Examiner—Paul F. Shaver
Attorney, Agent, or Firm—Wenderoth, Lind & Ponack

[57] ABSTRACT

A process for preparing trialkylsilyldiazomethanes in which halomethyltrialkylsilane represented by the general formula $R^1R^2R^3SiCH_2X$ (wherein $R^1$, $R^2$ and $R^3$ denote an alkyl group of 1 to 4 carbon atoms, and X denotes a halogen group) is reacted with metallic magnesium to give a Grignard reagent, which is then reacted with diphenyl phosphoric acid azide.

17 Claims, No Drawings

PROCESS FOR PREPARING TRIALKYLSILYLDIAZOMETHANES

BACKGROUND OF THE INVENTION (1) Field of the Invention

This invention relates to a novel process for the synthesis of trialkylsilyldiazomethanes.

(2) Description of the Prior Art

Trialkylsilyldiazomethanes are useful reagents which are employed in the improved synthesis process of ArndtEistert proposed by the same inventors of this invention (Japanese patent application Nos. Sho 55-87564 and Sho 55-140887), the homologation reaction process (Japanese patent application No. Sho 55-87565), the process for the preparation of nitro-$\beta$-trialkylsilylstyrene oxide (Japanese patent application No. Sho 55-87566) and the novel synthesis process of carboxylic acid ester (Japanese patent application No. Sho 56-17725), etc., and the following procedures are already known, in which trimethylsilyldiazomethane is adopted as an example.

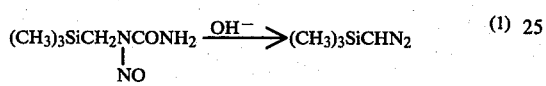    (1)

Journal of Organometallic Chemistry, 44, 279 (1972)

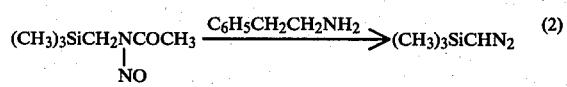    (2)

Synthesis, 1976, 271

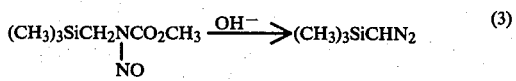    (3)

Zhurnal Obshchei Khimii, 39, 2785 (1969)

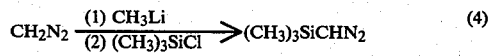    (4)

Chemical Communication, 1967, 836; Journal of Chemical Society, (A) 2954 (1970)

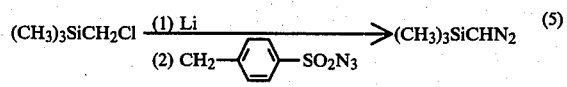    (5)

Synthesis and Reactivity in Inorganic and Metal-Organic Chemistry, 9, 297 (1979)

Yields of these procedures are, however, poor, such as (1) 56%, (2) 30%, (3) 25%, (4) 5% and (5) 38%, thus there are many practical problems.

SUMMARY OF THE INVENTION

An object of the present invention is to provide a process for preparing trialkylsilyldiazomethane with a high yield.

In accordance with the process of this invention, trialkylsilyldiazomethane (IV) is prepared by a process in which halomethyltrialkylsilane (I) represented by the general formula $$R^1R^2R^3SiCH_2X$$

wherein
$R^1$, $R^2$ and $R^3$ denote an alkyl group of 1 to 4 carbon atoms, and
X denotes a halogen group,
is reacted with metallic magnesium to give a Grignard reagent (II), which is then reacted with diphenyl phosphoric acid azide (III).

DETAILED DESCRIPTION OF THE INVENTION AND THE PREFERRED EMBODIMENTS

The above-mentioned reactions are illustrated by the following equation:

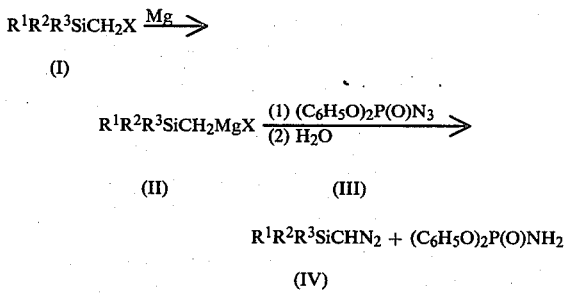

The reaction of halomethyltrialkylsilane (I) with metallic magnesium is carried out by introducing metallic magnesium into a solvent, activating it with 1,2-dibromoethane or iodine, etc., and thereafter adding halomethyltrialkylsilane (I) with refluxing the solvent. The amount of metallic magnesium used in the reaction may be in the range of from 1 to 2 mols and preferably is from 1 to 1.5 mols per mol of halomethyltrialkylsilane (I). If the amount of the metallic magnesium is too little, unreacted silane (I) remains and is liable to exert a bad influence upon the next reaction. Too much metallic magnesium does not exert a desirable influence upon the current reaction and only results in a loss of the magnesium. The reaction temperature may be from 0° C. to 150° C. and preferably is from 0° C. to 70° C. Too low a temperature is undesirable due to a small reaction rate, while too high a temperature is liable to bring about bumping and therefore is undesirable. Reaction time may be from 30 minutes to 48 hours, preferably from 1 to 24 hours.

The reaction of the Grignard reagent obtained by the above-mentioned reaction with diphenyl phosphoric acid azide(III) may be carried out in the solvent at a temperature between $-78°$ C. and 40° C. for a reaction time between 10 minutes and 48 hours, preferably between 30 minutes and 48 hours. Reaction temperatures lower than $-78°$ C. are difficult to attain commercially, while those higher than 40° C. are liable to bring about decomposition of diphenyl phosphoric acid azide (III). Too short a reaction time is insufficient for the progress of reaction, while too long a time is uneconomical. The amount of diphenyl phosphoric acid azide (III) used may be from 0.8 to 2 mols, preferably from 0.9 to 1.2 mols per mol of the Grignard reagent. Too small an amount or too large an amount of the azide (III) results in an immoderate loss of the Grignard reagent or azide (III) and therefore is undesirable.

As the solvents used in the reaction according to this invention, ether type solvents such as diethyl ether, di-n-butyl ether and tetrahydrofurane, etc. are employed. After the end of the reaction, the reaction solution is worked up with ice water, etc. to obtain trialkylsilyldiazomethane generally in its solution form. The solution can be employed as such for various reactions.

As concrete compounds of halomethyltrialkylsilane (I) used in this invention, there may be mentioned chloromethyltrimethylsilane, chloromethyltriethylsilane, chloromethyltripropylsilane, chloromethyldimethylethylsilane and chloromethyldimethyl-t-butylsilane, etc. There also may be mentioned other corresponding halogen compounds than the above mentioned chlorocompounds.

A characteristic of this invention is that trialkylsilyldiazomethane can be obtained with a remarkably high yield as compared with the hitherto known processes.

This invention is illustrated by the following examples.

EXAMPLE 1

To a mixed solution of metallic magnesium (0.875 g, 36 mmol) and diethyl ether (2 ml), a drop of 1,2-dibromoethane was added with stirring to activate magnesium, and thereafter further diethyl ether (10 ml) was added. A solution of chloromethyltrimethylsilane (3.678 g, 30 mmol) in diethyl ether (8 ml) was then added dropwise at such a rate that the solvent would be refluxed. After the dropwise addition, the reaction solution was stirred for 20 hours at the room temperature to prepare a Grignard reagent.

To a solution of diphenyl phosphoric acid azide (7.425 g, 27 mmol) in diethyl ether (40 ml), the abovementioned Grignard reagent was added dropwise at 0° C. After the dropwise addition, the reaction solution was stirred at 0° C. for 2 hours and at the room temperature for 3 hours. The reaction solution was added to ice water to separate precipitates, which were filtered with suction and washed with diethyl ether, and then the filtrate diethyl ether layer and diethyl ether washings were combined, washed with cold water and dried (anhydrous sodium sulphate). Diethyl ether was subjected to an atmospheric concentration (bath temperature being below 45° C.) using Widmer's fractional distillation device. The remaining solution was distilled under a reduced pressure (15 mmHg) at a bath temperature of 0° C.–30° C. and collected with cooling by dry ice-acetone to obtain yellow liquid, which was further subjected to an atmospheric concentration to obtain 4.098 g of yellow solution of trimethylsilyldiazomethane in diethyl ether.

According to NMR spectrum, the yield of trimethylsilyldiazomethane was 78.6% and its concentration was 59.1 weight % (g/g).

EXAMPLE 2

Example 1 was followed with same amounts of reagents, reaction conditions and working-up process, except that the synthesis of the Grignard reagent was carried out at the room temperature for 3 hours and the reaction of diphenyl phosphoric acid azide with the Grignard reagent was carried out at 0° C. for 2 hours.

About 5 ml of a solution of trimethylsilyldiazomethane in diethyl ether was obtained. 10 ml of hexane was added to this solution and diethyl ether was completely distilled off under the normal pressure using Widmer's distillation device to obtain 11.27 ml of yellow solution of trimethylsilyldiazomethane in hexane.

According to NMR spectrum, the yield of trimethylsilyldiazomethane was 75.3% and its concentration was 1.805 mol/l.

EXAMPLE 3

To a mixture of metallic magnesium (0.875 g, 36 mmol) and di-n-butyl ether (2 ml), a drop of 1,2-dibromoethane was added with stirring to activate magnesium, and thereafter further di-n-butyl ether (10 ml) was added. A solution of chloromethyltrimethylsilane (3.678 g, 30 mmol) in di-n-butyl ether (8 ml) was then added dropwise in such a manner that the reaction temperature was 30°–40° C. After the dropwise addition, it was stirred for 3 hours at 30° C. to prepare a Grignard reagent.

To a solution of diphenyl phosphoric acid azide (7.425 g, 27 mmol) in di-n-butyl ether (40 ml), the abovementioned Grignard reagent was added dropwise at 0° C. After the dropwise addition, the reaction solution was stirred at 0° C. for 1.5 hours. The reaction solution was added to ice water to separate precipitates, which were filtered with suction and washed with di-n-butyl ether, and then the filtrate di-n-butyl ether layer and di-n-butyl ether washings were combined, washed with cold water and dried (anhydrous sodium sulphate). Thereafter, it was distilled under a reduced pressure (a bath temperature of 45°–48° C., 15 mmHg) until yellow color of the distillate disappeared. The distillate was further distilled under a reduced pressure (a bath temperature of 87°–94° C., 90–103 mmHg) using Widmer's fractional distillation device to obtain 1.857 g of yellow solution of trimethylsilyldiazomethane in di-n-butyl ether.

According to NMR spectrum, the yield of trimethylsilyldiazomethane was 55.3% and its concentration was 91.8 weight % (g/g).

EXAMPLE 4

Example 3 was followed with same amounts of reagents, reaction conditions and working-up process, except that the synthesis of Grignard reagent was carried out at 30° C. for 2 hours and at the room temperature for 17 hours and the reaction of diphenyl phosphoric acid azide with the Grignard reagent was carried out at 0° C. for 2 hours and at the room temperature for 3 hours. 1.848 g of solution of trimethylsilyldiazomethane in di-n-butyl ether was obtained.

According to NMR spectrum, the yield of trimethylsilyldiazomethane was 57.6% and its concentration was 96.1 weight % (g/g).

EXAMPLE 5

To a mixed solution of metallic magnesium (292 mg, 12 mmol) and tetrahydrofurane (1 ml), a drop of 1,2-dibromoethane was added with stirring to activate magnesium, and thereafter further tetrahydrofurane (3 ml) was added. A solution of chloromethyltrimethylsilane (1.24 g, 10 mmol) in tetrahydrofurane (3 ml) was then added dropwise in such a manner that the reaction temperature was 30°–35° C. After the dropwise addition, it was stirred at the room temperature for 3 hours to prepare a Grignard reagent.

To a solution of diphenyl phosphoric acid azide (2.48 g, 9 mmol) in tetrahydrofurane (10 ml), the abovementioned Grignard reagent was added at −5°–0° C. After the dropwise addition, it was stirred at 0° C. for 2 hours. After 20 ml of ice water was added to the reaction solution, it was distilled under a reduced pressure (15 mmHg, a bath temperature of 0° C.-30° C.) to obtain a solution of trimethylsilyldiazomethane in tetrahydrofurane. Hexane (7 ml) was added, and the solution was washed with cold water until tetrahydrofurane disappeared, and was thereafter dried (anhydrous sodium sulphate). 7.31 ml of yellow solution of trimethylsilyldiazomethane in hexane was obtained.

According to NMR spectrum, the yield of trimethylsilyldiazomethane was 57.6% and its concentration was 0.7 mol/l.

COMPARISON EXAMPLE

To a mixed solution of metallic magnesium (1.050 g, 43.2 mmol) and diethyl ether (5 ml), a drop of 1,2-dibromoethane was added with stirring to activate magnesium, and thereafter further diethyl ether (15 ml) was added. A solution of chloromethyltrimethylsilane (4.414 g, 36 mmol) in diethyl ether (5 ml) was then added dropwise at such a rate that the solvent was refluxed. After the dropwise addition, the reaction solution was stirred at 25°-30° C. for 19 hours to prepare a Grignard reagent.

To a solution of tosylazide (para-toluenesulfonylazide) (6.383 g, 32.4 mmol) in diethyl ether (100 ml), the above-mentioned Grignard reagent was added dropwise at 0° C. for 1 hour. After the dropwise addition, the reaction solution was stirred at 0° C. for 6 hours and at the room temperature for 34 hours. Precipitates separated were filtered with suction and washed with diethyl ether, and then the filtrate and washings were combined, washed with cold water and with cold aqueous 1% caustic soda solution and dried (anhydrous sodium sulphate).

Diethyl ether was subjected to an atmospheric concentration (bath temperature being below 45° C.) using Widmer's fractional distillation device, and the remaining solution was distilled under a reduced pressure (15 mmHg) at a bath temperature of 0° C.-30° C. and collected with cooling by dry ice-acetone. Yellow liquid obtained was further subjected to an atmospheric concentration to obtain 1.51 g of yellow solution of trimethylsilyldiazomethane in diethyl ether.

According to NMR spectrum, the yield of trimethylsilyldiazomethane was 16.7% and its concentration was 40.9 weight % (g/g).

Results are shown in the Table below.

What is claimed is:

1. A process for preparing a trialkylsilyldiazomethane, which comprises reacting halomethyltrialkylsilane represented by the formula $$R^1R^2R^3SiCH_2X$$

wherein $R^1$, $R^2$ and $R^3$ denote an alkyl group of 1 to 4 carbon atoms and X denotes a halogen group, with metallic magnesium to give a Grignard reagent, and reacting the Grignard reagent with diphenyl phosphoric acid azide.

2. A process according to claim 1, wherein the amount of said metallic magnesium is from 1 to 2 mols per mol of said halomethyltrialkylsilane.

3. A process according to claim 1, wherein the amount of said metallic magnesium is from 1 to 1.5 mols per mol of said halomethyltrialkylsilane.

4. A process according to claim 1, wherein the reaction of said halomethyltrialkylsilane with said metallic magnesium is conducted at a temperature from 0° C. to 150° C.

5. A process according to claim 1, wherein the reaction of said halomethyltrialkylsilane with said metallic magnesium is conducted at a temperature from 0° C. to 70° C.

6. A process according to claim 1, wherein the reaction of said halomethyltrialkylsilane with said metallic magnesium is conducted for a time from 30 minutes to 48 hours.

7. A process according to claim 1, wherein the reaction of said halomethyltrialkylsilane with said metallic magnesium is conducted for a time from 1 to 24 hours.

8. A process according to claim 1, wherein the amount of said diphenyl phosphoric acid azide is from 0.8 to 2 mols per mol of said Grignard reagent.

9. A process according to claim 1, wherein the amount of said diphenyl phosphoric acid azide is from 0.9 to 1.2 mols per mol of said Grignard reagent.

10. A process according to claim 1, wherein the reaction of said Grignard reagent with said diphenyl phosphoric acid azide is conducted in a solvent at a temperature between −78° C. and 40° C.

11. A process according to claim 10, wherein said reaction with said diphenyl phosphoric acid azide is conducted for a time between 10 minutes and 48 hours.

12. A process according to claim 10, wherein said reaction with said diphenyl phosphoric acid azide is conducted for a time between 30 minutes and 48 hours.

TABLE

| | Solvent | Azide | Synthesis of Grignard reagent | | Reaction with azide | | Yield (%) | Concentration*1 (%) |
|---|---|---|---|---|---|---|---|---|
| | | | temp. | time | temp. | time | | |
| Example 1 | diethyl ether | III | room temp., | 20 hr. | 0° C. / room temp., | 2 hr. / 3 hr. | 78.6 | (59.1) |
| Example 2 | diethyl ether | III | room temp., | 3 hr. | 0° C., | 2 hr. | 75.3 | (1.805 mol/l)*2 |
| Example 3 | di-n-butyl ether | III | 30° C., | 3 hr. | 0° C. | 1.5 hr. | 55.3 | (91.8) |
| Example 4 | di-n-butyl ether | III | 30° C., / room temp., | 3 hr. / 17 hr. | 0° C., / room temp. | 2 hr. / 3 hr. | 57.6 | (96.1) |
| Example 5 | tetrahydrofurane | III | room temp., | 3 hr. | 0° C., | 2 hr. | 57.6 | (0.71 mol/l)*2 |
| Comparison example | diethyl ether | tosyl azide | room temp., | 19 hr. | 0° C., / room temp. | 6 hr. / 34 hr. | 16.7 | (40.9) |

*1 Concentrations are expressed in weight % (g/g) except for the case of being described in mol/l
*2 in hexane 13. A process according to claim 1, wherein both of said reactions are carried out in a solvent.

14. A process according to claim 1, wherein both of said reactions are carried out in an ether solvent.

15. A process according to claim 14, wherein said ether solvent is selected from the group consisting of diethyl ether, di-n-butyl ether and tetrahydrofurane.

16. A process according to claim 1, wherein said halomethyltrialkylsilane is selected from the group consisting of chloromethyltrimethylsilane, chloromethyltriethylsilane, chloromethyltripropylsilane, chloromethyldimethylethylsilane and chloromethyldimethyl-t-butylsilane.

17. A process according to claim 1, wherein said halomethyltrialkylsilane is chloromethyltrimethylsilane.

* * * * *